United States Patent [19]

Suzuki et al.

[11] Patent Number: 5,491,082
[45] Date of Patent: Feb. 13, 1996

[54] PLASMINOGEN ACTIVATOR COVALENTLY BONDED TO A POROUS BODY OF β-TRICALCIUM PHOSPHATE

[75] Inventors: Takahiro Suzuki, Nagoya; Sukezo Kawamura, Inuyama; Motohiro Toriyama, Kasugai; Yoshiyuki Yokokawa; Yukari Kawamoto, both of Nagoya; Yasuharu Hakamatsuka; Hiroyuki Irie, both of Hachioji, all of Japan

[73] Assignees: Director-General of Agency of Industrial Science and Technology; Olympus Optical Co., Ltd., both of Tokyo, Japan

[21] Appl. No.: 246,940

[22] Filed: May 20, 1994

Related U.S. Application Data

[63] Continuation-in-part of Ser. No. 852,550, Mar. 17, 1992, abandoned.

[30] Foreign Application Priority Data

Mar. 18, 1991 [JP] Japan ..................... 3-077202

[51] Int. Cl.⁶ ..................... C12N 11/14; C12N 9/72; A61K 38/48
[52] U.S. Cl. .................. 435/176; 435/215; 424/94.63
[58] Field of Search ..................... 435/177, 176, 435/180, 215

[56] References Cited

U.S. PATENT DOCUMENTS

| | | | |
|---|---|---|---|
| 4,282,324 | 8/1981 | Neidleman et al. | 435/168 |
| 4,423,149 | 12/1983 | Amon, Jr. et al. | 435/132 X |
| 4,737,411 | 4/1988 | Graves, Jr. et al. | 428/403 |
| 4,764,466 | 8/1988 | Suyama et al. | 435/174 X |
| 4,778,471 | 10/1988 | Bajpai | 623/16 |
| 5,037,749 | 8/1991 | Findlay | 435/176 |

FOREIGN PATENT DOCUMENTS

| | | |
|---|---|---|
| 60-106459 | 6/1985 | Japan . |
| 62-65222 | 2/1987 | Japan . |
| 64-40418 | 2/1989 | Japan . |
| 1-197429 | 8/1989 | Japan . |

OTHER PUBLICATIONS

Zaborsky, O., Immobilized Enzymes, CRC Press, Cleveland, Ohio, 1973, p. 75.

*Primary Examiner*—David M. Naff
*Attorney, Agent, or Firm*—Frishauf, Holtz, Goodman, Langer & Chick

[57] ABSTRACT

A plasminogen activator such as urokinase or tissue plasminogen activator is covalently bonded to a porous body composed of calcium phosphate to form a plasminogen activator-porous body complex. The tricalcium phosphate can be α-tricalcium phosphate, β-tricalcium phosphate, hydroxyapatite, tetracalcium phosphate, octacalcium phosphate and mixtures thereof. In a preferred embodiment, β-tricalcium phosphate which has excellent biocompatibility with the body or a mixture of β-tricalcium phosphate and hydroxyapatite is used. Preferably, synthetic calcium phosphate is used is to avoid impurities contained by natural calcium phosphate. Covalent bonding is by crosslinking with glutaraldehyde, bismaleimides, dihalogenic aryls or diisocyanates, or by using cyanogen bromide, diazotization or periodic acid. The complex can be filled into a column to form a bioreactor. A granular complex can be intravascularly injected into the blood of a patient to provide thrombotic activity for a long period of time. In another embodiment, a complex of a predetermined shape can be implanted to provide thrombotic activity.

4 Claims, No Drawings

PLASMINOGEN ACTIVATOR COVALENTLY BONDED TO A POROUS BODY OF β-TRICALCIUM PHOSPHATE

This application is a Continuation-In-Part, of application Ser. No. 07/852,550 filed Mar. 17, 1992, now abandoned.

BACKGROUND OF THE INVENTION

1. Field of the Invention

The present invention relates to a complex of a plasminogen activator and a porous body (to be referred to as a plasminogen activator-porous body complex hereinafter).

2. Description of the Related Art

A plasminogen activator is a factor for activating plasminogen and converting it into plasmin as one of anti-coagulation factors of blood components. This plasminogen activator, for example, is intravascularly injected in a patient of thrombosis as a thrombotic agent.

The plasminogen activator loses its activity within a short period of time by a plasminogen activator inhibitor present in the blood of a patient when the plasminogen activator is intravascularly injected. The plasmin activated by the plasminogen activator also loses its thrombotic activity by the behavior of the plasmin inhibitor in the blood. For this reason, in order to obtain a sufficient thrombotic activity, a large amount of plasminogen activator must be intravascularly injected.

When purification of the plasminogen activator is not perfectly performed, impurities such as proteins and peptide chains other than plasminogen are mixed in the plasminogen activator. As a result, in intravascular injection of a large amount of plasminogen activator, a serious side effect may be caused, thus endangering the patient.

SUMMARY OF THE INVENTION

It is an object of the present invention to provide a plasminogen activator-porous body complex which can maintain the activity of a plasminogen activator for a long period of time.

More specifically, the present invention provides a plasminogen activator-porous body complex wherein a plasminogen activator is covalently bonded to a porous body comprising a calcium phosphate series material.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

DETAILED DESCRIPTION OF THE PREFERRED EMBODIMENTS

In a plasminogen activator-porous body complex (to be referred to as a complex hereinafter) according to the present invention, examples of the calcium phosphate series material constituting the porous body are α-tricalcium phosphate, β-tricalcium phosphate, hydroxylapatite, tetracalcium phosphate, octacalcium phosphate, and a mixture consisting of at least two of the above materials. Of all the materials, a-tricalcium phosphate, β-tricalcium phosphate, hydroxylapatite, and a mixture thereof are particularly preferable because they are excellent in biological affinity. Calcium phosphate series material can be obtained in two ways. One way is to obtain calcium phosphate as a natural material derived from pulverized bones of living creatures such as birds, animals, and fish as shown, for example, in U.S. Pat. No. 5,037,749. The other is to obtain calcium phosphate as a chemically synthesized material as described in U.S. Pat. No. 4,717,556.

In the present invention, the calcium phosphate series material is used as a carrier, to which the plasminogen activator is bound, to be embedded in a human body. Therefore, natural calcium phosphate is not suitable for the above-mentioned usage since it is difficult to avoid contamination with impurities. For this reason, synthetic calcium phosphate is desirable. The chemically synthesized calcium phosphate is used in embodiments described below.

Examples of the plasminogen activators are urokinase and tissue plasminogen activator.

A method of immobilizing a plasminogen activator on a porous body is not limited to a specific one if it includes an immobilizing technique of an enzyme through a covalent bond. For example, an immobilizing method such as a crosslinking method of an enzyme and a carrier with a difunctional agent (e.g., glutaraldehyde, bismaleimides, dihalogenic aryls, and diisocyanates), a cyanogen bromide method, a diazotization method, or a periodic acid method can be used. Of these methods, the crosslinking method of an enzyme and a carrier with glutaraldehyde, i.e., a glutaraldehyde method is most preferable.

In a complex according to the present invention, a plasminogen activator is immobilized on a porous body comprising a calcium phosphate series material excellent in biocompatibility. The complex can maintain the activity of the plasminogen activator for a long period of time. Therefore, the present invention can provide new applications such as bioreactor obtained by filling a column with the complex and intravascular injection of a granulated complex. When the complex is intravascularly injected, the plasminogen activator immobilized on the complex is rarely affected by its inhibitor. Therefore, a sufficient effect can be obtained with a small dose.

Embodiments of the present invention will be described in detail below.

EMBODIMENT 1

A complex obtained by coating urokinase as a plasminogen activator on a porous body consisting of β-tricalcium phosphate will be described below.

A carrier consisting of a porous body of β-tricalcium phosphate (to be referred to as a β-TCP carrier hereinafter) used in this embodiment was evaluated for biocompatibility by a tissue culture test using a human fetal renal cell as follows.

The β-tricalcium phosphate porous body can be produced according to processes described in the literature for example U.S. Pat. No. 5,152,791.

A human fetal renal cell (cell name: 293 Cell available from Dainippon Pharmaceutical Co. Ltd.) attached to the β-TCP carrier in an Eagle MEM medium containing 10% fetal bovine serum was cultured in a $CO_2$ incubator (concentration: 5% $CO_2$) at 37° C. The medium was drawn and removed from the petri dish. The β-TCP carrier having the cells attached thereon was washed with a phosphate buffer to remove floating cells. A trypsin solution was reacted with the β-TCP carrier having the cells for three minutes. Thereafter, the phosphate buffer was gently sprayed to the reacted product using a pipet to remove the cells from the β-TCP carrier.

Upon completion of the tissue culture as described above, the number of cells grown on the carrier, i.e., a growing cell number, a specific growth rate, and a mass of cell protein were measured.

The total number of cells attached to the β-TCP carrier was calculated by a counting chamber and a Coulter counter. The growing cell number was obtained by a trypan blue dyeing method. The specific growth rate (μ) was calculated by equation (1) below using the number of cells in logarithmic growth from the second day to the fifth day of the culture:

$$\mu = (1/N_{a.cell}) \cdot d_{Na.cell}/dt \quad (1)$$

where $N_{a.cell}$ is the total number of cells attached to the β-TCP carrier.

The mass of the cell protein attached to the β-TCP carrier was measured as follows. The β-TCP carrier obtained upon the tissue culture was washed with a phosphate buffer, and 2 ml of 0.5N sodium hydrate were added thereto to dissolve the cells attached to the β-TCP carrier. The concentration of the protein in the solution was measured by a Lowly method using bovine serum albumin as a standard protein.

As a comparative example, a human fetal renal cell was attached to a plastic culture dish (Lux), and a tissue culture was performed and a growing cell number, a specific growth rate, a mass of a cell protein were measured following the same procedures as described above.

The growing cell number, the specific growth rate, and the mass of the cell protein in the β-TCP carrier had differences from the culture using the plastic culture dish (Lux) within 10%. As a result, it was confirmed that the β-TCP carrier was excellent in biocompatibility.

An example of covalent bonding of urokinase to a β-TCP carrier by a glutaraldehyde method will be described below.

From 2 to 5 g (dry weight) of a β-TCP carrier having a diameter of about 100 to 500 μm were put in a 500 ml Erlenmeyer flask. One hundred milliliter of a 2 vol % aminoprophyl triethoxy silane/toluene solution were added in the Erlenmeyer flask. A Liebig condenser was then attached to the Erlenmeyer flask, and the solution was refluxed under heating in an oil bath at 110° C. for 6 hours.

The β-TCP carrier was washed with about 50 ml of toluene using a glass filter and a Buchner flask and was dried at 60° to 100° C.

Thereafter, 100 mg of the dried β-TCP carrier were filled in a glass column. Quartz glass wool was filled on the upper and lower surfaces of the β-TCP carrier using a Pasteur pipet (inner diameter: 5 mm), thereby holding the β-TCP carrier.

Ten milliliter of a 0.01M phosphate buffer (pH 7) containing 2.5 wt % of glutaraldehyde were circulated in the column at 4° C. using a peristalyic pump, and 50 ml of a 0.01M phosphate buffer were circulated for 24 hours to wash the carrier. In this case, the pump flow rate was set at 6 ml/min.

Ten milliliter of a 0.01M phosphate buffer containing urokinase (0.01 mg/ml) were then circulated in the column at 4° C. for 24 hours to coat the urokinase on the β-TCP carrier.

The urokinase-coated β-TCP carrier was sequentially washed with 10 ml of a 0.5M sodium chloride/1M phosphate buffer mixed solution and 20 ml of a 0.01M phosphate buffer to remove the non-bonded urokinase, thereby obtaining an urokinase-β-TCP complex in which urokinase is immobilized with a covalent bond onto the surface of the porous β-TCP carrier including the inside surface of the pores.

The urokinase-β-TCP complex thus prepared was filled in the column, and a pseudo body fluid containing 10% serum was continuously supplied. The plasmin activity in the fluid was maintained at high level as long as 100 hours or more.

When the urokinase-β-TCP complex was granulated and intravascularly injected, a thrombosis or a thrombosis precursor could be resolved and eliminated.

At this time, since urokinase is immobilized on the β-TCP porous body with a covalent bond so as to coat the entire surface including the inside pore surface thereof, the urokinase activity of the β-TCP porous body is hardly inactivated by a plasminogen activator inhibitor in the blood. Therefore, the thrombotic activity in the blood was maintained for a long period of time. In addition, since the β-TCP carrier is excellent in biocompatibility, the human body is not much affected by the carrier even if the granulated complex is intravascularly injected.

When the urokinase-β-TCP complex was formed into a predetermined shape and was implanted in a human body, the urokinase was gradually dispersed to obtain the same effect as described above.

EMBODIMENT 2

A tissue culture test using a human fetal renal cell and a carrier consisting of a hydroxylapatite porous body (to be referred to as HAP carrier hereinafter) was conducted following the same procedures as in Embodiment 1. The test result was compared with a case in which cells were cultured in a plastic culture dish (Lux). In comparison with the test results obtained using a plastic culture dish, the growing cell number, the specific growth rate, and the mass of a cell protein had differences within 10%. It was thus confirmed that the HAP carrier was excellent in biocompatibility.

Urokinase was covalently bonded to an HAP carrier by a glutaraldehyde method following the same procedures as in Embodiment 1 to prepare an urokinase-HAP complex.

This urokinase-HAP complex was filled in a column, and a pseudo body fluid containing 10% serum was continuously supplied thereto. The plasmin activity in the fluid was maintained at high level as long as 200 hours or more.

EMBODIMENT 3

A tissue culture test using a human fetal renal cell and a carrier consisting of a tricalcium phosphate porous body containing 8 wt % of hydroxylapatite (to be referred to as HAP/β-TCP carrier hereinafter) was conducted following the same procedures as in Embodiment 1. The test result was compared with a case in which cells were cultured in a plastic culture dish (Lux). In comparison with the test results obtained using a plastic culture dish, the growing cell number, the specific growth rate, and the mass of a cell protein had differences within 10%. It was thus confirmed that the HAP/β-TCP carrier was excellent in biocompatibility.

Urokinase was covalently bonded to an HAP/β-TCP carrier by a glutaraldehyde method following the same procedures as in Embodiment 1 to prepare an urokinase-HAP/β-TCP complex.

This urokinase-HAP/β-TCP complex was filled in a column, and a pseudo body fluid containing 10% serum was continuously supplied thereto. The plasmin activity in the fluid was maintained at high level as long as 140 hours or more.

In Embodiments 1 to 3, urokinase was immobilized on a porous body. However, a tissue plasminogen activator can be immobilized in the same manner as described above.

What is claimed is:

1. A plasminogen activator-porous body complex comprising:

a porous body comprising a chemically synthesized β-tricalcium phosphate; and a plasminogen activator covalently bonded to the porous body;

said complex being formed by the process comprising:

immersing said porous body in a dilute solution of a plasminogen activator and covalently bonding said plasminogen activator to said porous body.

2. The complex according to claim 1, wherein said porous body comprises a mixture of β-tricalcium phosphate and hydroxylapatite.

3. The complex according to claim 1, wherein said plasminogen activator is selected from the group consisting of urokinase and a tissue plasminogen activator.

4. The complex according to claim 1, wherein said covalent bonding of said plasminogen activator to the porous body is by crosslinking with glutaraldehyde, bismaleimides, dihalogenic aryls or diisocyanates; or by using cyanogen bromide diazotization; or periodic acid.

* * * * *